(12) United States Patent
Abrami (10) Patent No.: US 10,939,974 B2
(45) Date of Patent: Mar. 9, 2021

(54) CLAMPING DEVICE

(71) Applicant: KIRMED FORNITURE OSPEDALIERE S.R.L., Muggia (IT)

(72) Inventor: Federico Abrami, Muggia (IT)

(73) Assignee: KIRMED FORNITURE OSPEDALIERE S.R.L., Muggia (IT)

( * ) Notice: Subject to any disclaimer, the term of this patent is extended or adjusted under 35 U.S.C. 154(b) by 0 days.

(21) Appl. No.: 16/490,350

(22) PCT Filed: Mar. 2, 2018

(86) PCT No.: PCT/IT2018/050033
§ 371 (c)(1),
(2) Date: Aug. 30, 2019

(87) PCT Pub. No.: WO2018/158791
PCT Pub. Date: Sep. 7, 2018

(65) Prior Publication Data
US 2020/0015921 A1    Jan. 16, 2020

(30) Foreign Application Priority Data

Mar. 3, 2017 (IT) .................. 102017000024029

(51) Int. Cl.
| | |
|---|---|
| *A61B 50/20* | (2016.01) |
| *A61M 5/00* | (2006.01) |
| *A61M 25/02* | (2006.01) |
| *A61B 50/00* | (2016.01) |

(52) U.S. Cl.
CPC ............ *A61B 50/20* (2016.02); *A61M 5/008* (2013.01); *A61M 25/02* (2013.01); *A61B 2050/002* (2016.02); *A61M 2025/024* (2013.01)

(58) Field of Classification Search
CPC .. A61B 50/20; A61B 2050/002; A61M 5/008; A61M 25/02; A61M 2025/024; F16B 2/26; F16B 2/22; F16B 9/023
See application file for complete search history.

(56) References Cited

U.S. PATENT DOCUMENTS

| | | | |
|---|---|---|---|
| 3,682,180 A | 8/1972 | McFarlane | |
| 3,980,263 A * | 9/1976 | Okuda | F16L 3/12 248/73 |
| 4,250,880 A * | 2/1981 | Gordon | A61M 25/02 128/DIG. 26 |
| 4,606,735 A | 8/1986 | Wilder et al. | |

(Continued)

FOREIGN PATENT DOCUMENTS

| | | |
|---|---|---|
| DE | 1851657 U | 5/1962 |
| EP | 1437812 A1 | 7/2004 |

(Continued)

OTHER PUBLICATIONS

International Search Report and Written Opinion from PCT/IT2018/050033 dated Jun. 25, 2018 (9 pages).

*Primary Examiner* — Ko H Chan
(74) *Attorney, Agent, or Firm* — Calfee Halter & Griswold LLP (57) ABSTRACT

A clamping device for objects comprises a flexible support plate that has a first surface suitable to be rested on a supporting surface or on the body of a patient, and a second surface, opposite the first surface, from which at least a pair of clamping members in the form of shaped platelets extend.

20 Claims, 3 Drawing Sheets

(56) References Cited

U.S. PATENT DOCUMENTS

| | | | | |
|---|---|---|---|---|
| 4,917,340 | A * | 4/1990 | Juemann | F16L 3/13 248/74.2 |
| 5,078,467 | A * | 1/1992 | Blomgren | G02B 6/3806 385/56 |
| 5,530,787 | A * | 6/1996 | Arnett | G02B 6/3887 385/137 |
| 5,947,931 | A * | 9/1999 | Bierman | A61M 25/02 128/DIG. 26 |
| 6,134,754 | A * | 10/2000 | Hansson | A61M 25/02 24/115 R |
| 6,467,742 | B1 * | 10/2002 | Pitcher | A47G 1/0611 248/205.3 |
| 6,554,489 | B2 * | 4/2003 | Kent | G02B 6/3829 385/135 |
| 7,001,081 | B2 * | 2/2006 | Cox | G02B 6/3887 385/86 |
| 7,784,745 | B2 * | 8/2010 | Dodge | F16L 3/1075 248/73 |
| 7,918,828 | B2 * | 4/2011 | Lundgaard | A61M 25/02 604/174 |
| 8,157,222 | B1 * | 4/2012 | Shirey | H02G 3/32 248/74.1 |
| 9,360,649 | B2 * | 6/2016 | Chang | G02B 6/4478 |
| 9,895,486 | B1 * | 2/2018 | Carey-Hench | A61M 16/0683 |
| 10,665,368 | B2 * | 5/2020 | Doye | H02G 3/32 |
| 2010/0247041 | A1 * | 9/2010 | Szilagyi | G02B 6/3887 385/86 |
| 2013/0053785 | A1 | 2/2013 | Parvatiyar et al. | |

FOREIGN PATENT DOCUMENTS

| | | |
|---|---|---|
| GB | 879109 A | 10/1961 |
| JP | 2004023817 A | 1/2004 |

\* cited by examiner fig. 10 fig. 7 fig. 8 fig. 9

CLAMPING DEVICE

CROSS-REFERENCE TO RELATED APPLICATIONS

This application is a 371 of PCT Application No. PCT/IT2018/050033 filed on Mar. 2, 2018, which claim priority to Italian Application No. 102017000024029 filed on Mar. 3, 2017, the contents of which are hereby incorporated by reference as if recited in their entirety.

FIELD OF THE INVENTION

The present invention concerns a clamping device which allows to clamp objects or instruments, easily and temporarily, on flat, inclined, or moving surfaces, preventing them from slipping to the ground.

The present invention is applied particularly, for example, in operating theaters, and can be used to temporarily clamp objects or medical instruments such as scalpels, syringes, or electro-medical handpieces, during the execution of surgical operations on a patient.

In particular, the clamping device according to the invention allows to position the objects quickly and repeatedly, inserting and removing them from the clamping device easily even with just one hand.

BACKGROUND OF THE INVENTION

In operating theaters there has always been a need to temporarily clamp objects or instruments that are used during the execution of an operation on a patient.

In fact, surgeons often have to use a plurality of instruments, depending on the type and progress of the surgical procedure, instruments that are usually provided and/or possibly replaced by specialized operators.

Because of the plurality of instruments that are used, the need is increasingly felt to have clamping devices that allow the surgeon to rest and clamp some of these instruments temporarily and autonomously while using others.

Solutions are known which provide to use magnetic plates which, resting on the operating field, allow to position and clamp instruments with magnetic properties, that is to say, metallic objects.

Such solutions, however, are becoming less and less useful, since an increasing majority of surgical instruments are made of plastic material, or non-magnetic metal material, so that they are not able to cooperate with the magnetic plates.

Solutions are also known that provide to use adhesive strips with Velcro, which once they have been made to adhere on the cloth of the operating field, allow to house and clamp only the cables of the electro-medical instruments inside the Velcro itself.

However, these solutions do not allow an easy repositioning of the electro-medical instrument.

Solutions are also known that provide to use non-woven fabric or plastic laminated pockets with an adhesive side, which are positioned on the vertical lateral surfaces of the operating field. The pockets allow to temporarily and easily house instruments or objects inside them.

However, these solutions are inconvenient to hold and clamp electro-medical instruments since, as they are equipped with a power supply cable, do not find adequate positioning in the pocket.

Numerous surgical instruments are connected by means of a cable to a machine through which they are driven and powered. Due to the weight of the cable to which they are connected, if not effectively clamped they can fall to the ground, with consequent problems of breaking the instrument and loss of sterility.

From the U.S. Pat. No. B4,606,735 a device is known for holding, in a desired position, a flexible tube connected to a medical device inserted in a patient, suitable to deliver or remove fluids into/from the patient. The holding device comprises a flexible strip provided with fins which develop upward and provided with perforated seatings aligned in an axial direction, in which the tube can be inserted. The device can comprise a component of a Velcro-type attachment member while the other component can be attached on a patient by means of an adhesive. This solution only allows to position tubes of a size suitable to be inserted in the holed seatings, and cannot be used to clamp in position instruments or devices having different shapes and sizes. Moreover, the shape of the seatings, while allowing a stable positioning of the tube, is not suitable to allow rapid insertion and extraction thereof, so it is not very efficient for holding and clamping medical instruments that have to be continuously supported and picked up again. Moreover, the particular configuration, inclined toward the inside with respect to the flexible strip, does not allow an operator to insert the tube in the seatings provided in the fins, without the latter being held by the operator himself. This therefore requires the operator to act with two hands on the holding device, an aspect which is particularly disadvantageous.

In a completely different field of the art, and for different applications with respect to those of the present invention, clamping devices for electric cables are also known from documents DE-U-18 51 657, EP-A-1 437 812 and JP-A-2004/023817, for an orderly, stable and precise positioning of the cables, preventing them from overlapping or twisting with each other. These devices allow rapid insertion of the cables inside them, but are configured to prevent an equally rapid removal thereof, so as to keep them constrained in the desired position. These solutions, therefore, are not suitable when it is necessary to temporarily clamp medical instruments in them which then have to be picked up quickly and repeatedly.

One purpose of the present invention is to obtain a clamping device which can be used to temporarily and easily clamp a plurality of objects or instruments, with or without a power supply cable.

Another purpose of the present invention is to obtain a clamping device that is economical and easy to manufacture, and which can be used on different surfaces, and several times.

Another purpose is to obtain a clamping device that can be sterilized and used in medical environments or operating theaters.

Another purpose is to obtain a clamping device totally free of metal parts so that it does not have to be removed if it is necessary to carry out an x-ray on the patient.

Another purpose is to obtain a light clamping device, easy to handle, which is low cost and therefore replaceable without economic problems.

The Applicant has devised, tested and embodied the present invention to overcome the shortcomings of the state of the art and to obtain these and other purposes and advantages.

SUMMARY OF THE INVENTION

The present invention is set forth and characterized in the independent claim, while the dependent claims describe other characteristics of the invention or variants to the main inventive idea.

In accordance with the above purposes, a clamping device according to the invention comprises a support plate that has a first surface suitable to be rested on a plane or a supporting surface, and a second surface, opposite the first surface, from which clamping members in the form of shaped platelets extend.

According to some embodiments, the support plate is made of flexible material so as to be able to adapt to flat or undulating support surfaces.

According to a variant, the clamping device can be at least partly made of thermoplastic or silicone polymer.

According to possible variants, the clamping device can comprise magnetic bands or segments, cooperating with the support plate, which allow to attach the clamping device on planes at least partly made of metal or magnetic material.

According to some embodiments, the shaped platelets are each disposed on a plane orthogonal with respect to the support plate, in particular to the second surface of the latter.

According to one aspect of the invention, each shaped platelet is elastically flexible.

The combination of the orthogonal position and the flexibility of the shaped platelets allows to be able to repeatedly insert and remove an object into/from the clamping device without needing the operator to act on the shaped platelets or to hold the support plate. These operations can therefore be carried out even with only one hand.

In accordance with the present invention, the shaped platelets have a profile with at least one hollow and a protruding portion, defining a concavity facing, during use, toward the support plate. The protruding portion in particular is configured to bend and deform so as to hold the objects to be clamped.

According to some embodiments, the clamping device comprises a first group and at least a second group of shaped platelets disposed aligned along respective positioning axes parallel to each other, so that the concavities of the shaped platelets of the first group and of the second group define between them a housing compartment aligned along a longitudinal axis, interposed between the two positioning axes and configured to house and hold the objects to be clamped.

According to other embodiments, the shaped platelets of the first and second group are disposed aligned in a herringbone pattern on the respective two positioning axes with respect to the longitudinal axis; said groups can consist of coherent or alternate rows.

According to other embodiments, the lying planes of the shaped platelets are inclined with respect to the longitudinal axis by an angle comprised between 10° and 80°. The angle of inclination, combined with the flexibility of the shaped platelets, promotes the rapid insertion and removal of the object to be clamped in/from the housing compartment.

These characteristics render the clamping device according to the present invention particularly suitable for application in the medical field to hold medical instruments, for example handpieces or similar instruments used by a surgeon in the operating theater. However, the clamping device according to the invention can be advantageously used to hold a plurality of objects of different types, for example, screw drivers, spanners, pens, pencils, scissors, or other instruments, tools, or objects preferably having an oblong development.

According to some embodiments, the shaped platelets of the first group and of the second group are facing each other with respect to the longitudinal axis.

According to a variant, the shaped platelets are disposed so that the respective protruding portions are facing the longitudinal axis.

According to some embodiments, the ends of the protruding portions of the shaped platelets of one row or group, can be substantially in contact with the ends of the protruding portions of the shaped platelets of the other row or group.

According to some embodiments, the two ends of two opposite shaped platelets with respect to the longitudinal axis are distanced from each other, for example by a distance correlated to the size of the objects that have to be clamped and as a function of the application of the clamping device.

According to some embodiments, the shaped platelets have a flat development on the respective lying plane.

According to some embodiments, the shaped platelets have a reduced thickness with respect to their extension sizes on the lying plane, for example less than 20% or even 10% of these, so that they are able to deform only with the application of the weight force of the object to be clamped, for example a medical instrument, in order to allow a rapid insertion and a rapid removal of the latter into/from the clamping device.

The conformation of the shaped platelets in particular allows them to deform in any direction, both along a longitudinal axis of the support plate and in a direction transverse to it.

According to some embodiments, the shaped platelets can have a second internal lower protruding portion, disposed substantially parallel to the first protruding portion, intermediate between the latter and the support plate.

According to some embodiments, the shaped platelets can also have several lower protruding portions, disposed parallel to the first protruding upper portion, intermediate between the latter and the support plate.

The shaped platelets define, with the respective connection portions, a central compartment in which the object to be held can be positioned.

According to some embodiments, at least the shaped platelets are made of a flexible material, so that the protruding portions can deform when an object is wedged into it, clamping it in position.

According to other embodiments, at least the internal lower second protruding portion can be provided with at least an incision, or at least a notch, which makes it more flexible in one direction, preferably in the direction of introduction and removal of the object to be held.

According to possible variant embodiments, it can be provided that the clamping device has a modular construction, and that it comprises two or more pairs of rows of shaped platelets, so as to define a plurality of compartments, each suitable to contain a respective object or instrument.

According to possible variants, the clamping device has attachment means, lateral or axial, so that it can connect with other clamping devices.

Embodiments of the present invention also concern a combination of a clamping device as described above and described hereafter, and at least one object inserted in the housing compartment of the clamping device.

In accordance with some embodiments of the invention, the object has a mainly oblong and at least partly rigid development.

BRIEF DESCRIPTION OF THE DRAWINGS

These and other characteristics of the present invention will become apparent from the following description of some embodiments, given as a non-restrictive example with reference to the attached drawings wherein.

To facilitate comprehension, the same reference numbers have been used, where possible, to identify identical common elements in the drawings. It is understood that elements and characteristics of one embodiment can conveniently be incorporated into other embodiments without further clarifications.

DETAILED DESCRIPTION OF SOME EMBODIMENTS

Embodiments described here with reference to FIGS. 1-5 concern a clamping device 10 which allows to easily and temporarily clamp objects 30 or instruments, in particular with sizes suitable for being handled by an operator.

By way of example, the clamping device 10 can be advantageously used to clamp objects 30 such as pens, pencils, scissors, screwdrivers, scalpels, syringes, pliers, handpieces and electro-medical probes, and suchlike, although it is not excluded that it can be used to clamp different objects or articles preferably having an oblong shape, for example endoscopes, or other instruments or tools.

The clamping device 10 according to the invention can preferably be applied in the medical sector, for example in operating theaters, even if other applications and uses are not excluded. The clamping device 10 can advantageously be used in work stations which require the use of several instruments, tools, and devices to perform certain operations, or suchlike.

The clamping device 10 allows to temporarily hold and clamp an object in a desired position, possibly also on inclined or moving planes, preventing it from sliding toward the ground.

The clamping device 10 comprises a support plate 12 provided with a first surface 13 suitable to be rested on a support surface, for example a work table, or an operating table, or, possibly, on a patient, and a second surface 14, opposite the first surface 13, on which a plurality of clamping members are disposed in the form of shaped platelets 16.

According to some embodiments, the support plate 12 is made of materials and sizes suitable to make it flexible, so as to be able to deform and adapt even to support surfaces which are not flat and which have undulations, hollows or protrusions.

According to preferred embodiments, the support plate 12 can be made by molding polymer material, for example polyurethane, or silicone materials. These materials can be sterilized, making the clamping device 10 suitable for use in medical rooms and operating theaters.

According to other embodiments, the thickness of the support plate 12 can be comprised, for example, between 2 mm and 8 mm depending on the type of material and its characteristics of flexibility and elasticity.

For example, in the case of polyurethane or silicone material, the thickness can be comprised between about 3 mm and about 5 mm.

According to some embodiments, on the first surface 13 an adhesive layer, for example a double-sided adhesive tape, or a glue can be applied, which allows to attach the clamping device 10 stably to the support surface on which it is rested.

This is particularly useful when the clamping device 10 is used in an operating theater, allowing it to be attached directly on a cloth or sheet of the operating field.

According to possible variants, it can be provided that the support plate 12 is provided with magnetic elements, for example magnetic bands or segments, possibly incorporated in the polymer material, which act as a magnet. In this way, the clamping device 10 can be attached to shelves or work surfaces having magnetic properties.

According to these embodiments, the magnetic bands or segments can be positioned distanced from each other, so as to allow the support plate 12 to bend and adapt even to non-flat support surfaces.

According to some embodiments, the shaped platelets 16 are made of flexible material and can bend and deform to adapt and hold the objects 30 to be clamped.

According to some embodiments, the shaped platelets 16 can be made of plastic material, for example, polyurethane, silicone material, or suchlike, which can be advantageously sterilized so as to make it suitable for use also in protected environments such as, for example, medical surgeries, operating theaters and sterile or pressurized chambers.

In particular, it can be provided that the clamping device 10 is completely made of polymer or plastic material, of the sterilizable type, so that it can also be used in magnetic resonance machines, or during the execution of X-rays on a patient, without having to remove it in advance.

The shaped platelets 16 can be stably attached to the support plate 12, or made in a single body with it.

According to some embodiments, the shaped platelets 16 are each disposed on a lying plane $\pi$ orthogonal to the second surface 14 of the support plate 12.

According to some embodiments, the shaped platelets 16 have a flat development on the respective lying plane $\pi$.

According to some embodiments, the clamping device 10 comprises at least one pair of shaped platelets 16 disposed facing one another.

According to some embodiments, the clamping device 10 comprises a first group 41 and a second group 42 of shaped platelets, disposed aligned along respective positioning axes X1, X2 parallel to one another.

According to some embodiments, the lying planes $\pi$ of the shaped platelets 16 are inclined with respect to the longitudinal axis X by an angle of inclination $\alpha 1$ comprised between 10° and 80°.

According to variant embodiments, the lying planes $\pi$ of the shaped platelets 16 are inclined with respect to the longitudinal axis X by an angle of inclination $\alpha 1$ comprised between 20° and 70°.

According to other variant embodiments, the lying planes $\pi$ of the shaped platelets 16 are inclined with respect to the longitudinal axis X by an angle of inclination $\alpha 1$ comprised between 30° and 60°.

The angle of inclination al can be chosen, for example, depending on the size of the objects 30 to be held.

According to some embodiments, the shaped platelets 16 of the first group 41 are facing those of the second group 42.

According to some embodiments, the shaped platelets 16 are positioned two by two in a specular manner with respect to a longitudinal axis X along the support plate 12 interposed between the two positioning axes X1, X2.

According to some embodiments, the shaped platelets 16 are disposed in a herringbone pattern on two rows with respect to the longitudinal axis X, forming between them an angle $\alpha 2$.

According to possible solutions, the angle $\alpha 2$ can be comprised between 20° and 160°, preferably between 40° and 140°.

According to preferred embodiments, the angle $\alpha 2$ can be comprised between about 60° and about 120°.

Advantageously, the herringbone disposition of the shaped platelets 16 defines a preferred position for the insertion and removal of the object 30 to be clamped, so as to render these operations quick and effective.

According to possible solutions, the shaped platelets 16 of the first group 41 are disposed symmetrical with respect to the shaped platelets 16 of the second group 42 along the longitudinal axis X.

According to possible variants, the shaped platelets 16 of the first group 41 are disposed alternately and offset with respect to the shaped platelets of the second group, along the longitudinal axis X.

According to some embodiments, the shaped platelets 16 have a profile with at least one recess and a protruding portion 20, 24, 25 to define a concavity 36 facing, during use, toward the second surface 14.

In particular, the concavities 36 of the shaped platelets 16 of the first group 41 and of the second group 42 define between them at least one housing compartment 22 for the object 30 to be held.

According to some embodiments, the housing compartment 22 is aligned along the longitudinal axis X, interposed between the two positioning axes X1, X2 of the first 41 and of the second group 42 of shaped platelets 16.

According to some embodiments described with reference to FIG. 1, the shaped platelets 16 comprise a connection portion 18 with the support plate 12, which extends in a direction substantially orthogonal to the second surface 14 and disposed in correspondence with the periphery of the support plate 12.

In this way, between the connection portions 18 of the shaped platelets 16 located respectively in one and the other row, the housing compartment 22 is defined in which the objects 30 to be clamped can be inserted.

The shaped platelets 16 also comprise at least a first protruding portion 20 which extends transversely to and above the connection portion 18, and having a free end 20a facing the inside of the support plate 12. The first protruding portions 20 are configured to perform the function of holding the objects 30 inserted in the housing compartment 22, deforming and closing on them.

According to possible embodiments, the upper protruding portion 20 can have a gradually decreasing section from the connection portion 18 toward the free end 20a, so as to be more flexible in correspondence with the central zone of the clamping device 10, and to facilitate the introduction/removal of the objects 30.

According to some embodiments, the ends of the upper protruding portions 20 of the shaped platelets 16 of one row can be substantially in contact with the ends of the upper protruding portions 20 of the shaped platelets 16 of the second row.

According to possible variants, the ends of the upper protruding portions 20 of the shaped platelets 16 of the two opposite rows are distanced by a distance correlated to the size of the objects 30 to be clamped.

The objects 30 can be inserted and removed from the clamping device 10 several times. To insert an object 30 into the clamping device 10 it is sufficient to press it against the upper protruding portions 20, with a pressure sufficient to deform them and define a passage opening up to the housing compartment 22. When the object 30 is positioned therein, the upper protruding portions 20 can return to their original shape, holding the object 30 positioned between them.

According to some embodiments, the shaped platelets 16 have a reduced thickness with respect to their sizes extending on the lying plane $\pi$, so as to be able to deform even only upon the application of the weight force of an object 30 to be clamped, in order to allow a rapid insertion and rapid removal of the latter into/from the clamping device.

By way of example, the shaped platelets 16 can have a thickness comparable to or less than that of the support plate 12, for example comprised between 1 mm and 5 mm, preferably comprised between 1 and 3 mm.

The reduced thickness and the conformation of the shaped platelets 16 allows them to be deformed in any direction, both along the longitudinal axis X and in a direction transverse thereto.

In this way it is possible to insert/remove the object 30 either by moving it in an axial direction in both senses along the longitudinal axis X, or by moving it with an upward and downward movement, and vice versa, along a plane orthogonal to the support plate 12, for example passing through the longitudinal axis X.

According to variant embodiments, described with reference to FIGS. 2-8, the shaped platelets 16 can also comprise at least one second internal lower protruding portion 24.

According to possible solutions, the second lower protruding portion 24 can extend at an intermediate height between the upper protruding portion 20 and the support plate 12.

According to possible solutions, the second lower protruding portion 24 can have an arched shape, having a first end connected to the connection portion 18 in proximity to the support plate 12, and a second free end located at an intermediate height between the support plate 12 and the upper protruding portion 20.

According to some embodiments, the second lower protruding portion 24 defines a second concavity 37 facing toward the support plate 12.

According to other embodiments, the upper protruding portion 20 and the lower protruding portion 24 can define a hollow between them, or a recess 25 defining another clamping member for the objects 30 to be clamped.

The presence of two protruding portions 20, 24 disposed at different heights with respect to the support plate 12 makes the device suitable to hold and clamp objects 30 or instruments of different sizes, in particular preventing them from slipping out of the housing compartment 22.

Figures 3, 4, 5, 6:
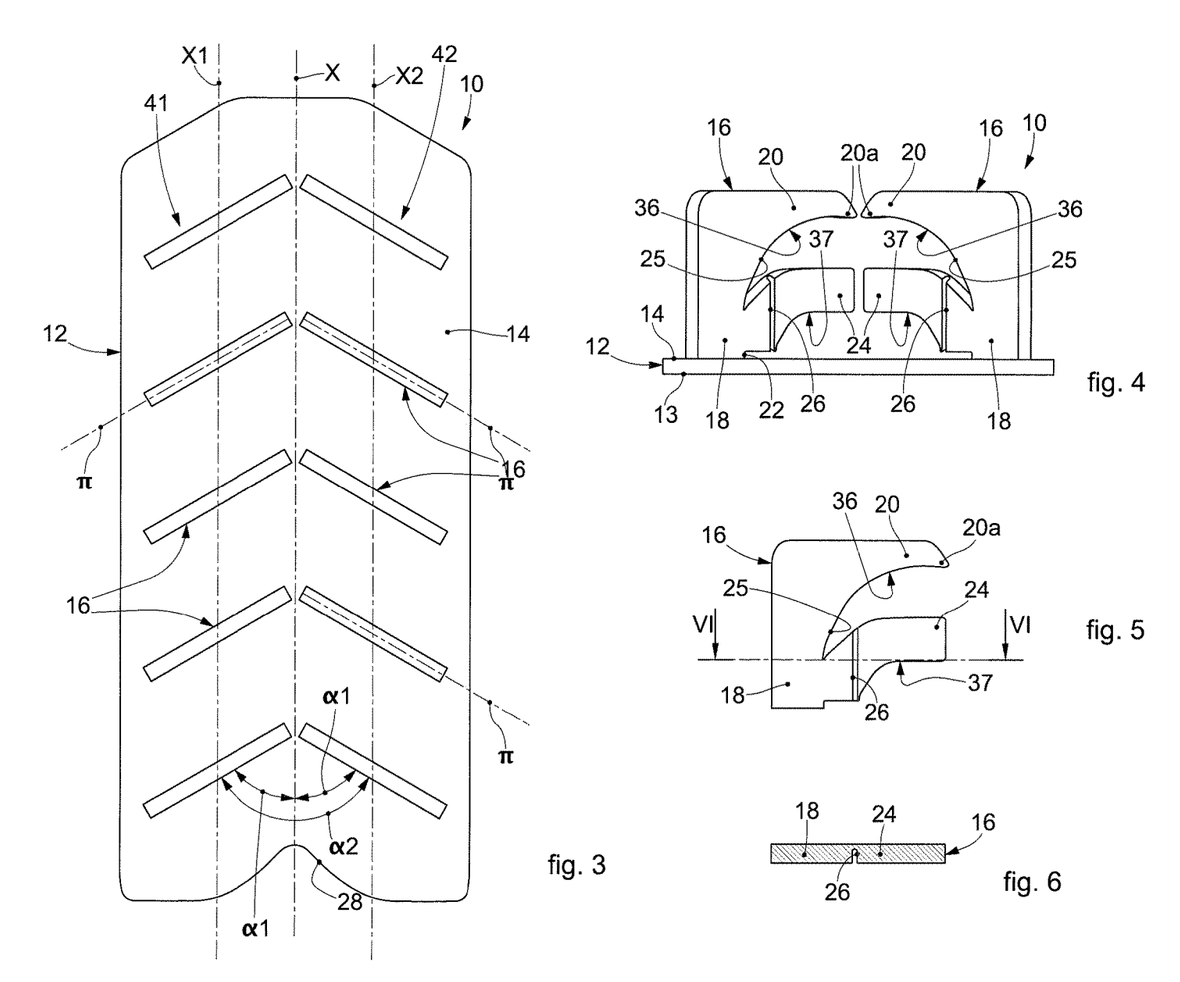
FIG. 3 is a plan view of a clamping device according to another variant embodiment.
FIG. 4 is a front view of the clamping device in FIG. 3.
FIG. 5 is a view in detail of a part of the device in FIG. 3.
FIG. 6 is a section view along the line VI-VI of FIG. 5.

According to other embodiments, shown by way of example in FIGS. 4 and 5, at least the lower protruding portion 24 can be provided with at least one incision 26, or a cut, configured to increase the flexibility of the lower protruding portion 24 and facilitate the introduction of the objects 30 to be clamped in the clamping device 10.

According to some embodiments, the incision 26 extends in a direction perpendicular to the support plate 12, and acts as a hinge to pivot the lower protruding portion 24 which can rotate with respect to it in the opposite direction to the face on which the incision 26 itself is present.

According to some embodiments, the incision 26 makes the lower protruding portion 24 more flexible in one direction, so as to define a univocal direction of use of the clamping device 10 which makes the introduction and removal of objects 30 into/from it faster and more effective.

The greater flexibility of the lower protruding portion 24 conferred by the incision 26 allows objects of greater size to be inserted all the way to the bottom of the housing compartment 22 of the clamping device 10, in contact with the second surface 14, and thus to be clamped better by the upper protruding portions 20.

The incision 26 on the lower protruding portion 24 also allows larger objects 30 to remain clamped in the clamping device 10, preventing the risk that they can be expelled therefrom due to lack of sufficient space at the bottom, or in proximity to the second surface 14.

According to some embodiments, the support plate 12 can have a rectangular shape, possibly with rounded corners, as shown by way of example in FIG. 3.

Figure 1:
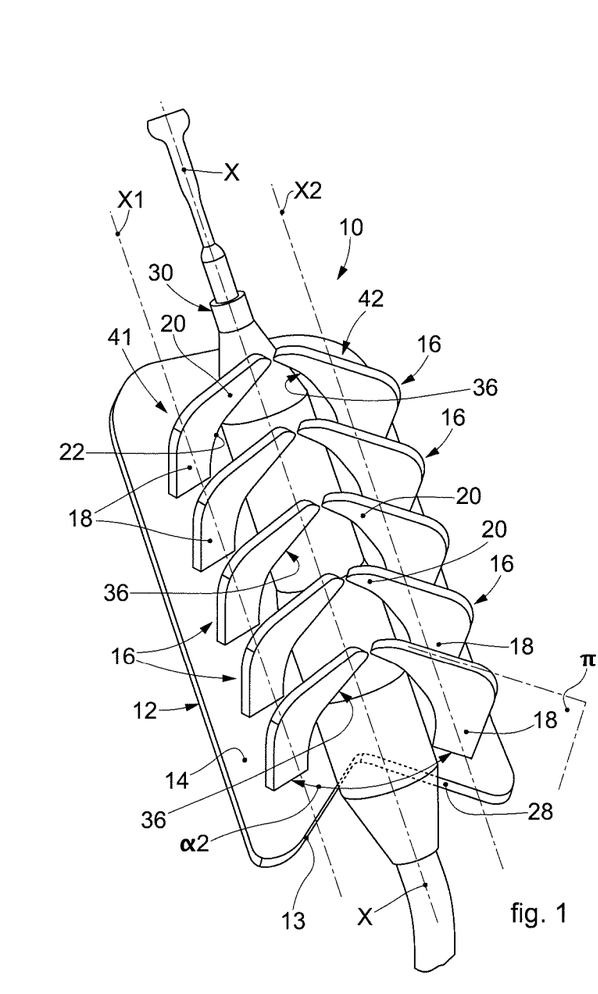
FIG. 1 is a perspective view of a clamping device in accordance with embodiments of the present invention.
Figure 2:
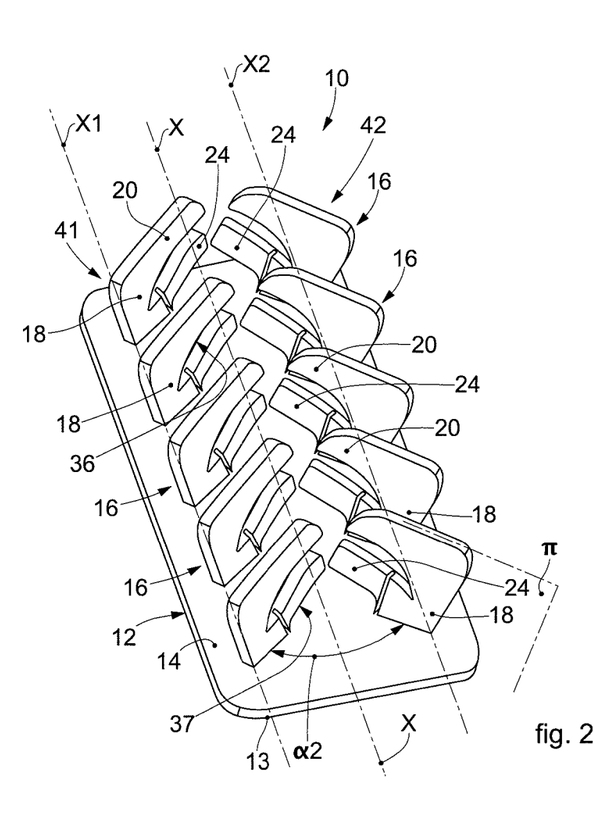
FIG. 2 is a perspective view of a clamping device according to a possible variant embodiment.

According to possible variants, for example shown in FIGS. 1 and 3, the support plate 12 can be provided, in the front portion, with a shaped profile provided with a recess 28 which can be more or less pronounced, which, if located in correspondence with an edge of the support surface, can facilitate the introduction/removal of the objects.

The recess 28 according to some embodiments can have edges with an inclination correlated with the inclination of the shaped platelets 16.

For example, in the case of objects 30 such as handpieces or other devices connected to a cable, the cable can be positioned in the recess 28, while the handpiece, or other device or object 30, is clamped in the clamping device 10.

The recess 28 can also contribute to indicate the best position of use of the clamping device 10, being preferably facing toward the operator.

Figure 7:
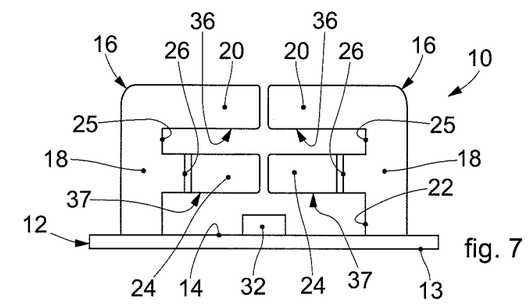
FIGS. 7-9 show front views of a clamping device in accordance with possible variant embodiments.

According to possible variant embodiments, shown for example in FIG. 7, it can be provided that the support plate 12 is provided with a protrusion, or a relief 32, disposed along the longitudinal axis X, which extends from the second surface 14. The protrusion 32 keeps the objects 30 to be clamped partly distanced from the support plate 12 itself, reducing the contact surface with the latter. This can be useful in the case of application of the clamping device 10 in an operating theater, where the objects 30 to be clamped could be soiled by biological fluids.

Figure 8:
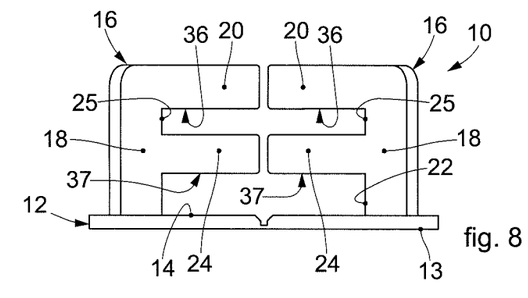
Figure 9:
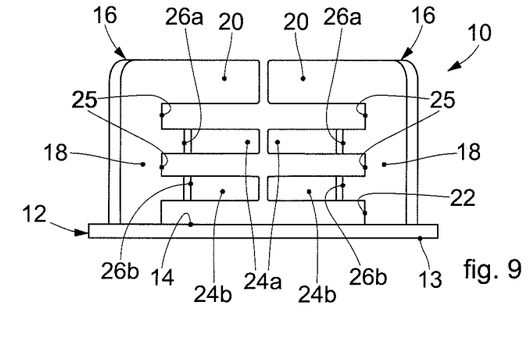

According to another variant, for example shown in FIG. 8, the support plate 12 can be provided with a hollow or groove 34, in which it is possible to collect any fluids and biological liquids present on the objects 30 to be clamped.

According to other embodiments, it can be provided that the shaped platelets 16 have several internal lower protruding portions 24a, 24b, which are flexible enough to bend and allow objects of different sizes to be housed inside the device 10.

According to some embodiments, it can be provided that the ends of the internal lower protruding portions 24a, 24b of respective opposite shaped platelets 16 are in contact with one another, or slightly distanced.

According to other embodiments, it can be provided that the internal lower protruding portions 24a, 24b are provided with incisions or cuts 26a, 26b substantially orthogonal to the support plate 12, or at most slightly inclined.

The incisions 26a, 26b can be more or less deep, and possibly in a different position on each of the internal lower protruding portions 24a, 24b, so as to define different levels of flexibility of the latter.

Figure 10:
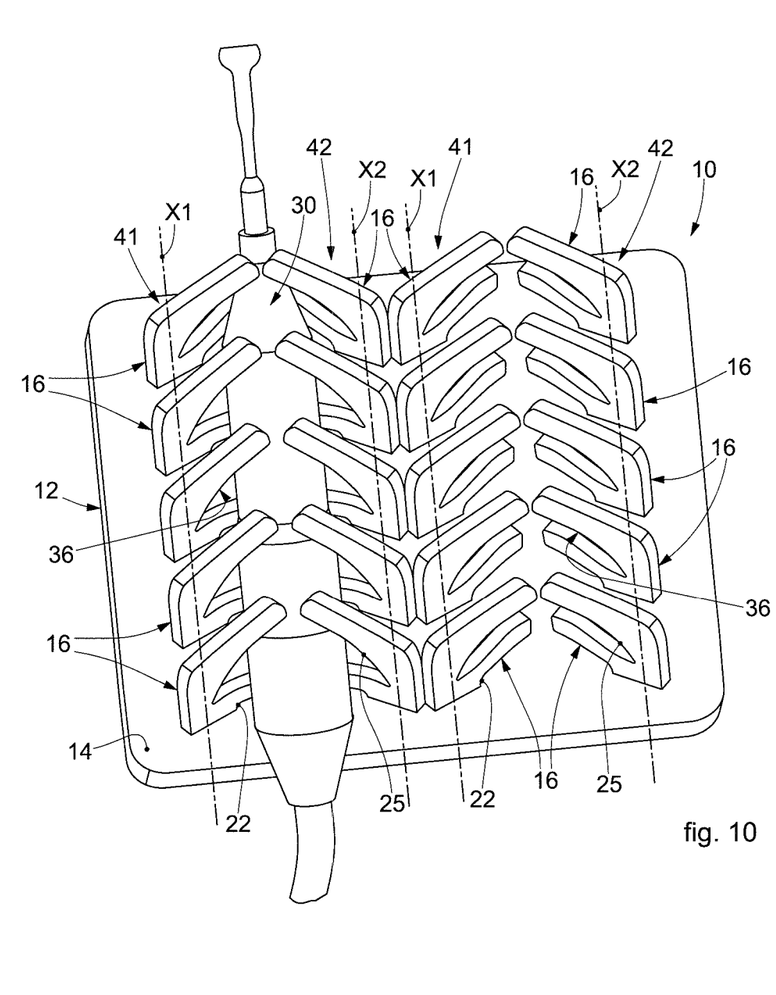
FIG. 10 is a perspective view of a clamping device according to another variant embodiment.

According to other embodiments, shown by way of example in FIG. 10, the clamping device 10 can comprise two or more pairs of groups of shaped platelets 16, disposed facing each other in twos, to define two or more housing compartments 22, each of them suitable to clamp at least one object 30.

According to other embodiments, it can be provided that the sizes of the shaped platelets 16 in the two pairs of groups are the same, or different, so as to define housing compartments 22 that are more or less big, and to make the clamping device 10 more versatile in relation to the type of object 30 to be clamped.

It is clear that modifications and/or additions of parts can be made to the clamping device 10 as described heretofore, without departing from the field and scope of the present invention.

It is also clear that, although the present invention has been described with reference to some specific examples, a person of skill in the art shall certainly be able to achieve many other equivalent forms of clamping device, having the characteristics as set forth in the claims and hence all coming within the field of protection defined thereby.

The invention claimed is:

1. Clamping device for objects, comprising a flexible support plate that has a first surface suitable to be rested on a supporting surface, or on the body of a patient, and a second surface, opposite the first surface, from which shaped platelets extend, wherein each of said shaped platelets is elastically flexible and lies on a lying plane orthogonal to said second surface, each of said shaped platelets having a profile with at least a hollow and a protruding portion to define a concavity facing, during use, toward said second surface, wherein said clamping device comprises a first group and at least a second group of said shaped platelets disposed aligned along respective positioning axes parallel to each other, the concavities of the shaped platelets of the first group defining with those of the second group at least a housing compartment aligned along a longitudinal axis, interposed between said positioning axes and configured to contain said objects, wherein said lying planes of said shaped platelets are inclined with respect to said longitudinal axis by an angle comprised between 10° and 80°.

2. Clamping device as in claim 1, wherein the shaped platelets of said first group are facing those of said second group.

3. Clamping device as in claim 1, wherein said shaped platelets have a flat development on the respective lying plane.

4. Clamping device as in claim 1, wherein each shaped platelet of said first group is inclined with respect to a respective shaped platelet of said second group by an angle with an amplitude comprised between 20° and 160°.

5. Clamping device as in claim 1, wherein the shaped platelets of said first group are disposed symmetrically with respect to the shaped platelets of said second group with respect to said longitudinal axis.

6. Clamping device as in claim 1, wherein the shaped platelets of said first group are disposed alternate and offset with respect to the shaped platelets of said second group along said longitudinal axis.

7. Clamping device as in claim 1, wherein said shaped platelets have a connection portion with the support plate and at least an upper protruding portion protruding from said connection portion, defining said concavity, configured to bend and deform so as to retain the objects to be clamped.

8. Clamping device as in claim 7, wherein said shaped platelets have a lower protruding portion, disposed in cooperation with said first upper protruding portion, intermediate between the latter and said support plate, defining a second concavity facing toward said support plate.

9. Clamping device as in claim 8, wherein at least said lower protruding portion is provided with at least an incision, or at least a notch.

10. Clamping device as in claim 1, wherein said support plate and said shaped platelets are made of silicone, polyurethane, or other sterilizable plastic material.

11. Clamping device as in claim 1, wherein said support plate has an adhesive layer in correspondence with said first surface.

12. Clamping device as in claim 1, wherein the clamping device comprises two or more pairs of groups of shaped platelets, disposed facing each other two by two to define two or more housing compartments, each suitable to clamp at least one object.

13. Combination of a clamping device as in claim 1 and at least one object of an oblong shape inserted in the housing compartment of said clamping device.

14. Clamping device as in claim 2, wherein said shaped platelets have a flat development on the respective lying plane.

15. Clamping device as in claim 14, wherein each shaped platelet of said first group is inclined with respect to a respective shaped platelet of said second group by an angle with an amplitude comprised between 20° and 160°.

16. Clamping device as in claim 15, wherein the shaped platelets of said first group are disposed symmetrically with respect to the shaped platelets of said second group with respect to said longitudinal axis.

17. Clamping device as in claim 15, wherein the shaped platelets of said first group are disposed alternate and offset with respect to the shaped platelets of said second group along said longitudinal axis.

18. Clamping device as in claim 17, wherein said shaped platelets have a connection portion with the support plate and at least an upper protruding portion protruding from said connection portion, defining said concavity, configured to bend and deform so as to retain the objects to be clamped.

19. Clamping device as in claim 18, wherein said shaped platelets have a lower protruding portion, disposed in cooperation with said first upper protruding portion, intermediate between the latter and said support plate, defining a second concavity facing toward said support plate.

20. Clamping device as in claim 19, wherein at least said lower protruding portion is provided with at least an incision, or at least a notch.

* * * * *